United States Patent [19]
Shin et al.

[11] Patent Number: 5,459,121
[45] Date of Patent: Oct. 17, 1995

[54] METHOD OF USING SORBITOL OR XYLITOL FOR PLANT WATER LOSS REDUCING AGENT

[75] Inventors: Charles C. Shin; Nicolai A. Favstritsky; Brent M. Sanders, all of Lafayette, Ind.

[73] Assignee: Great Lake Chemical Corporation, West Lafayette, Ind.

[21] Appl. No.: 230,624

[22] Filed: Apr. 21, 1994

[51] Int. Cl.$^6$ ............ A01N 43/08; A01N 43/16; A01N 31/02
[52] U.S. Cl. ............ 504/114; 504/292; 504/299; 504/353; 426/321
[58] Field of Search ............ 504/292, 299, 504/353, 114; 426/321; A01N 31/02

[56] References Cited

U.S. PATENT DOCUMENTS

| | | | |
|---|---|---|---|
| 4,125,393 | 11/1978 | Kohl et al. | 71/3 |
| 4,420,329 | 12/1983 | Laughlin | 71/122 |
| 5,298,482 | 3/1994 | Tanaka et al. | 504/320 |

*Primary Examiner*—S. Mark Clardy
*Attorney, Agent, or Firm*—Woodard, Emhardt, Naughton, Moriarty & McNett

[57] ABSTRACT

A method for reducing plant water loss by closing stomatal openings and reducing the transpiration rate. In particular, a water loss reducing composition made of an osmo-adjusting solute such as sorbitol or xylitol is applied to plants. The solution is applied to the root zone by drenching regularly or prior to water deficiency, and preferably includes between about 0.5 and about 25 weight percent of the water loss reducing and conditioning agent.

14 Claims, 12 Drawing Sheets

Abcission occurred at 7:00 am

METHOD OF USING SORBITOL OR XYLITOL FOR PLANT WATER LOSS REDUCING AGENT

FIELD OF THE INVENTION

The present invention relates generally to compositions and methods for reducing water loss of plants, and more particularly to compositions and methods for conditioning plants for water stress (drought stress) avoidance.

BACKGROUND OF THE INVENTION

Water is becoming increasingly precious worldwide. Twenty-five nations are now experiencing chronic water shortages, and that number will certainly increase as we move into the 21st Century. Further, because world agriculture must be able to provide food for more than 11 billion people by the year 2050, pressure on water resources will increase further as the global community attempts to triple its agriculture output while simultaneously reducing environmental concerns.

Water that is applied to plants is largely lost as run off, evaporation and/or transpiration. Unfortunately, because of the plant's inefficient systems of regulating water loss through transpiration, farmers are forced to apply large quantities of water to compensate for the water that is lost by the plants. The amount of water used by the plants for growth is considerably less than the amount that the plant takes up and eventually loses. The majority of the water that is lost by the plants is lost through the stomata or pores on the surfaces of the leaves.

There are two basic methods of reducing water loss through the stomata. First, water loss may be reduced by physically plugging up the stomatal openings with a surface applied large organic polymer. A number of compounds that reduce water loss by physically coating the surfaces have been tested, and some of these compounds, e.g., latex emulsions, are effective. However, the effects are specific to the plant and environmental conditions, and the effectiveness of these types of anti-transpirant depends on complete coverage of the plant surfaces by water molecules. Further, the application is messy and not practical.

Alternatively, water loss may be reduced by introducing compounds into the plant and causing the stomata to close physiologically. Compounds such as abscisic acid and high carbon dioxide are capable of closing stomata. However the effects have been quite temporary and/or inconsistent. It is difficult to manage effectively these compounds without detrimental effects to plant quality.

A need therefore exists for a plant water loss reducing agent which is non-toxic to the plants, environmentally acceptable and relatively inexpensive. The present invention addresses this need by providing methods and compounds for reduction of plant water loss and for conditioning plants for water stress avoidance.

SUMMARY OF THE INVENTION

Briefly describing one aspect of the present invention, there is provided a method for reducing plant water loss by closing stomatal openings and reducing the transpiration rate. The inventive method comprises applying to the plants an effective amount of an osmo-adjusting solute such as sorbitol or xylitol. The solution is applied to the root zone by drenching regularly or prior to water deficiency. The solution preferably includes between about 0.5 and about 25 weight percent of the water loss reducing and conditioning agent. The inventive water loss reducing agent is also shown to be effective for conditioning plants for water stress avoidance.

One object of the present invention is to provide compositions and methods for reducing water loss of plants.

Another object of the present invention is to provide compositions and methods for conditioning plants for avoidance of certain environmental arid handling stresses, such as those which occur in conjunction with transplanting, drought, soil water shortage, excessive salt concentration in soil media, and transportation.

A further object of this invention is to provide plant water loss reducing and conditioning compositions and methods which are relatively inexpensive, non-toxic and environmentally acceptable.

Further objects of the present invention will be apparent from the following description.

DESCRIPTION OF THE PREFERRED EMBODIMENT

Figure 1:
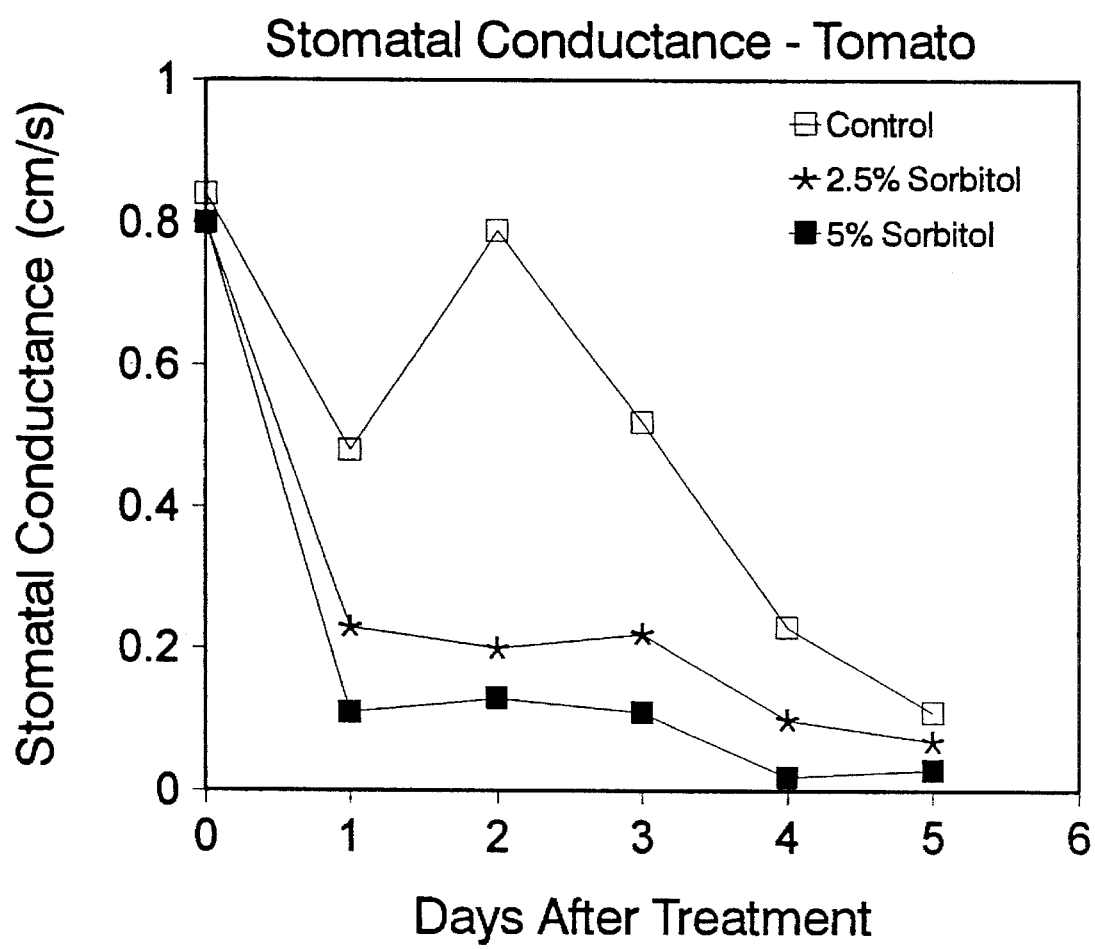
FIG. 1 is a graph of stomatal conductances over time, for tomato seedlings treated with aqueous solutions of 0%, 2.5%, and 5% sorbitol.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In accordance with this invention, novel plant water loss reducing and conditioning agents have been discovered comprising an aqueous solution containing a plant water loss reducing and conditioning component selected from the group consisting of osmo-adjusting solutes, their analogs, and mixtures thereof. Preferably, the composition comprises an aqueous solution comprising between about 0.05 and about 25 weight percent of the water loss reducing component and most preferably comprises between about 0.5 to 10 weight percent of the water loss reducing component. It has also been discovered that the water loss reducing composition is effective in conditioning the plant tissue for avoidance of water stress.

As used hereinafter, osmo-adjusting solutes are organic compounds that may be used to adjust osmolality of plant growth medium, especially to reduce water potential more negatively and thereby to reduce water loss of plants and plant tissues. Osmo-adjusting compounds include glycerol, sorbitol, xylitol, mannitol, arabitol, proline, aspartic acid, glutamic acid, betaine (glycinebetaine), and alaninebetaine.

All osmo-adjusting solutes and their analogs are acceptable for use in the present invention. Preferred osmo-adjusting solutes are polyols of the formula $CH_2OH(CHOH)_nCH_2OH$ where n=0 to 4. Also preferred are monosaccharides of the formula $(CH_2O)_n$ where n=3 to 6. Sorbitol and xylitol are most preferred for use in the present invention.

Sorbitol may be obtained from berries, cherries, plums, pears, apples, seaweeds or algae according to known techniques. It is prepared industrially from glucose by high pressure hydrogenation or electrolytic reduction, and is available to one of ordinary skill in the art without undue experimentation.

Xylitol is found as a natural intermediate in the metabolism of D-glucose through glucuronate cycle in livers. It is generally prepared by the reduction of xylose, and is used as oral and intravenous nutrient and in anti-caries preparations. Xylitol has an $LD_{50}$ in mice of approximately 22 grams/kilogram, and is available to one of ordinary skill in the art without undue experimentation.

Water loss of plants may be reduced by applying the water loss reducing compositions of the present invention by methods such as root drenching, ebb and flow, or drip irrigation. Alternatively, roots may be soaked directly in the water loss reducing composition. Any conventional apparatus suitable for root drenching may be employed. Depending on the degree of water loss reduction and conditioning desired, repeat applications may be appropriate. Second and subsequent applications are generally applied after intervals of up to one week.

Maximum water loss reduction differences between treated and non-treated plants are achieved in 24 hours after application of the composition. The degree of water loss reduction is a function of the degree of osmo-adjustment, which is a function of outside water stress induced by the concentration of the inventive compositions.

The compositions may be formulated and supplied to the user at the desired strength or in concentrated form and diluted to the desired strength prior to application to the plants. No special handling and mixing steps are required. However, since the active ingredient is a carbohydrate, prolonged storage should be avoided after the composition is formulated.

Although plants respond immediately to the treatment of tile present invention, it is preferred for some applications that the compositions include non-ionic surfactants. Suitable surfactants operate as spreading agents and otherwise may be inert, or at least non-interfering components. For example, two different surfactants, polyoxyethylene sorbitan monolaurate (Tween 20) and polyoxyglycol siloxane (Silwet 77) have been found not to interfere the effectiveness of the compositions in appropriate circumstances. When non-ionic surfactants are used, it is preferred that the composition contain between about 0.005 and about 0.5 weight percent of the non-ionic surfactant.

As indicated, the water loss reducing methods of the present invention are applicable for the treatment of plants desired to reduce water loss and to condition plants for desiccation avoidance. Accordingly, the inventive methods may further be applicable to a wide range of environmental and handling stresses, as well as to many types of plants and plant products.

The following examples will further illustrate the invention, with all percentages being by weight unless otherwise indicated. It will be appreciated that these examples are demonstrative only, and the applicability of the methods described herein extends to various other plants and plant products, as well as differing types of environmental and handling stresses.

EXAMPLE 1

The efficacy of the present invention is demonstrated by results showing reduction in transpiration rate of tomato plants. Water losses by transpiration of the tomato plants and by evaporation of the soil moisture were determined.

Two trays each containing ten young tomato seedlings along with another set of trays without plants were treated with an aqueous solution of 0.5% sorbitol and DI water. Each tray was weighed three days after the treatments. Average water losses of a tray without plants (water loss by evaporation only), a tray with 0.5% sorbitol treated plants (water loss by evaporation and transpiration), and a tray with DI water treated plants (water loss by evaporation and transpiration) were 26 grams/day, 37 grams/day, and 45 grams/day respectively. The transpiration rates per plant were 1.9 gram/day/plant for DI water treated plants and ½ grams/day/plant for sorbitol treated plants. The root-drenching with an aqueous solution of 5% sorbitol reduced the transpiration rate of young tomato seedling more than 35% as listed in Table 1.

TABLE 1

Solution Uptake and Water Loss of Tomato Plants Treated With Aqueous Solutions of 0% and 5% Sorbitol

| Treatments | | Solution Uptake (g) (for 1 hour Dip) | | Water Loss (g) |
|---|---|---|---|---|
| 1st | 2nd | 1st | 2nd | (for 3 days) |
| Sorbitol | Water | 146.9 | 88.0 | 109.2 (w/plants) |
| Sorbitol | Sorbitol | 171.6 | 97.7 | 114.8 (w/plants) |
| Water | Water | 163.5 | 136.7 | 135.1 (w/plants) |
| Sorbitol | Water | 136.8 | 66.7 | 88.0 (no plants) |
| Sorbitol | Sorbitol | 138.0 | 60.7 | 72.1 (no plants) |
| Water | Water | 134.2 | 79.4 | 74.3 (no plants) |

Note:
Trays were submerged in aqueous solutions of 0% and 5% sorbitol twice for one hour. The 2nd dip was made 3 days after the 1st.

Summary:
- Water loss of a tray without plants=26 g/day
- Water loss of a tray with plants dipped in water=45 g/day
- Water loss of a tray with plants in 5% sorbitol=37 g/day
- Average transpiration rate of a plant root drenched with water=1.9 g/day
- Average transpiration rate of a plant root drenched with 5% sorbitol

EXAMPLE 2

The effectiveness of the present invention on stomatal conductance in tomato, pepper, and cucumber seedlings was determined.

Figure 2:
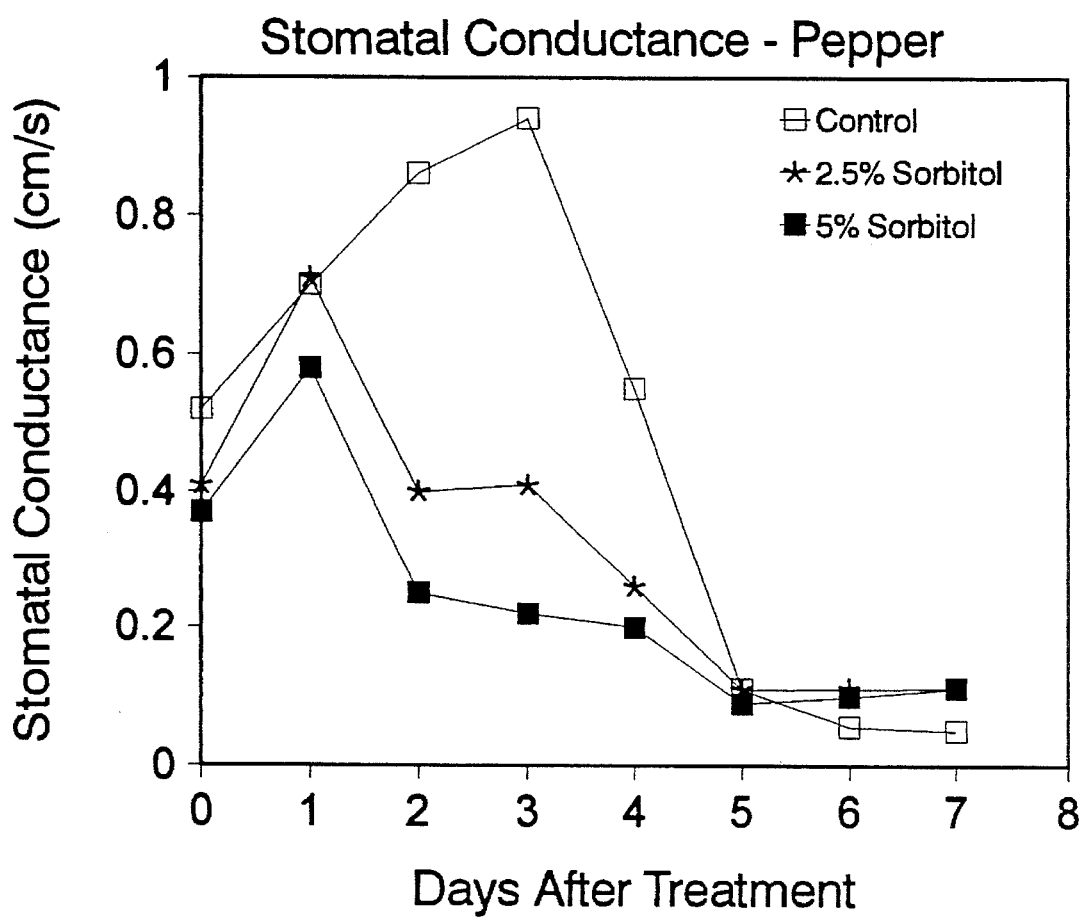
FIG. 2 graphically illustrates stomatal conductances of pepper seedlings treated with aqueous solutions of 0%, 2.5%, and 5% sorbitol.
Figure 3:
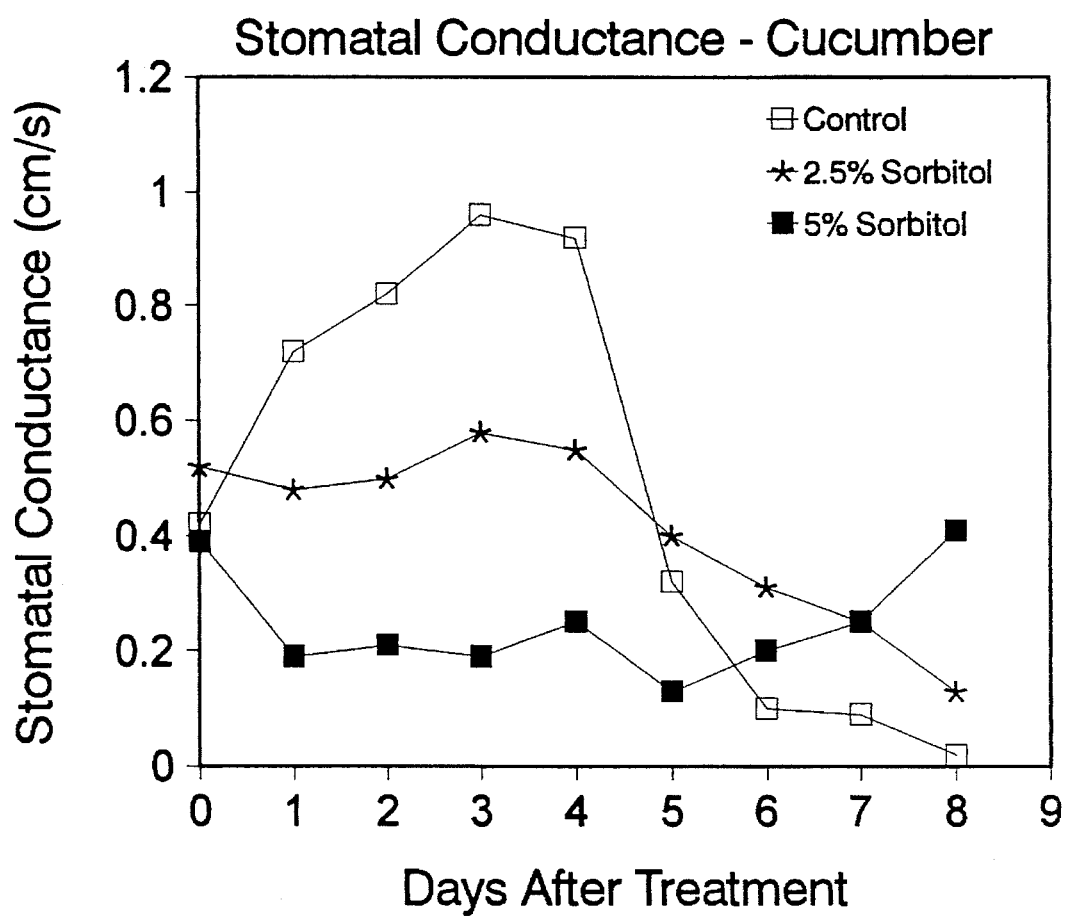
FIG. 3 graphically illustrates stomatal conductances of cucumber seedlings treated with aqueous solutions of 0%, 2.5%, and 5% sorbitol.

Tomato, pepper, and cucumber seedlings were treated with aqueous solutions of 2.5% and 5% sorbitol and stomatal conductances were determined every 24 hours after the treatment for five days. The results are shown in FIGS. 1–3.

The results show that treating plants with aqueous solutions of 2.5% and 5% sorbitol induces stomatal closure, indicating that the present invention is effective in inducing stomatal closing and reducing transpiration rates of tomato, pepper, and cucumber seedlings. The treated plants remained turgid and had greener leaves than the control plants. The effectiveness of tile present invention was observed within 24 hours after treatment.

EXAMPLE 3

The effectiveness of the present invention in reducing water loss of tomato, pepper, and cucumber plants was determined.

Figure 4:
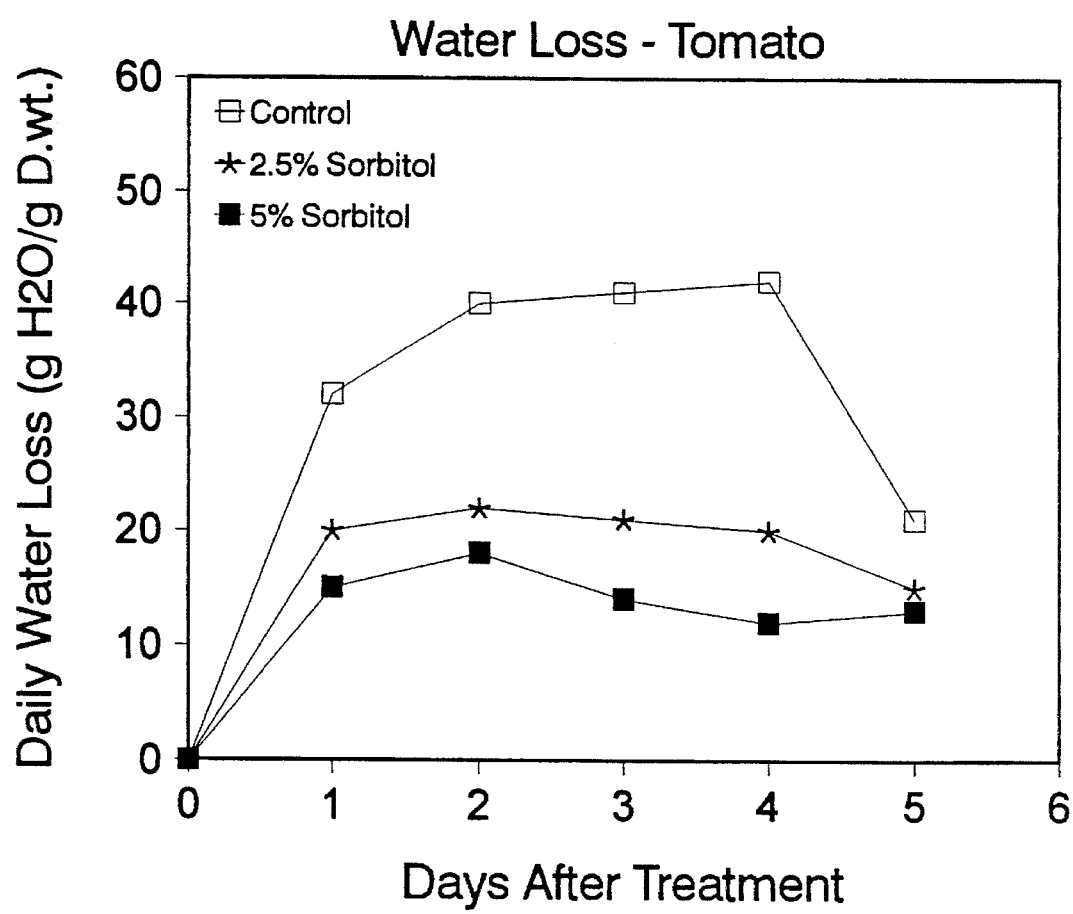
FIG. 4 graphically illustrates daily water loss for tomato seedlings treated with aqueous solutions of 0%, 2.5%, and 5% sorbitol.
Figure 5:
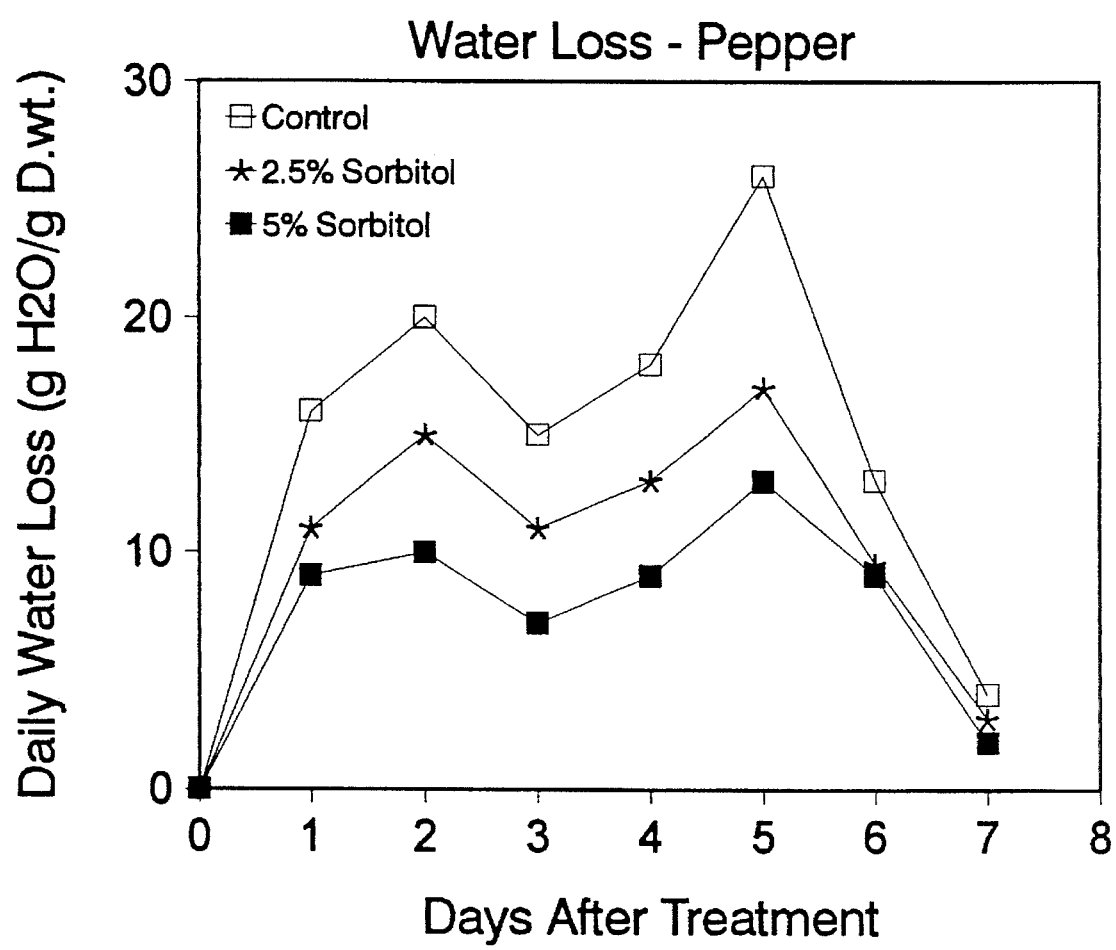
FIG. 5 graphically illustrates daily water loss for pepper seedlings treated with aqueous solutions of 0%, 2.5%, and 5% sorbitol.
Figure 6:
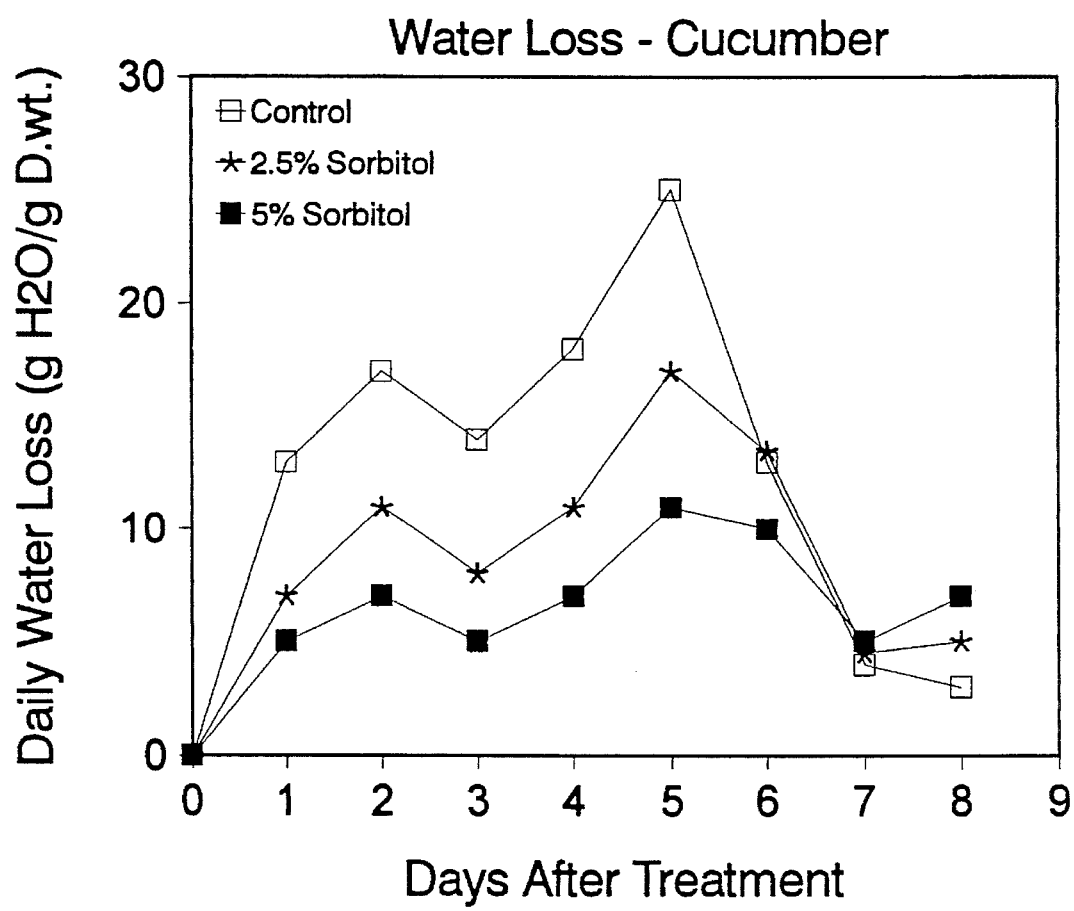
FIG. 6 graphically illustrates daily water loss for cucumber seedlings treated with aqueous solutions of 0%, 2.5%, and 5% sorbitol.

Tomato, pepper, and cucumber seedlings were treated with aqueous solutions of 0%, 2.5% and 5% sorbitol. After treatment, each pot was wrapped in a polyethylene bag tied at the base of stem to keep soil moisture from evaporating—allowing the plants to lose water through shoot tissue only. Each pot was weighed every 24 hours after the treatments for five days. Water loss of the plant was evaluated, and the results are shown in FIGS. 4–6.

The results indicate that treating plants with a composition of the present invention significantly reduces water loss by the plant, and that the reduction in water loss is greater for plants treated with an aqueous solution of 5% sorbitol than for plants treated with 2.5% sorbitol. The effectiveness of the present invention in reducing water loss was demonstrated on all species tested.

EXAMPLE 4

The effectiveness of the present invention is further demonstrated by experiments showing that the relative soil water content (RWC) and xylem water potential of treated plant is significantly greater than the relative soil water content and xylem water potential of controls.

Pepper seedlings grown in 5.5 cm×5.5 cm×6.5 cm pots were drenched with 50 ml aqueous solutions of 0%, 2.5% and 5% sorbitol. The excess solution to tile field capacity of the soil was drained away after drenching. The pots were then wrapped in a plastic bag and tied at the base of the stem to keep soil moisture from evaporating. The soil RWC and xylem water potential were determined seven days after the treatment. The soil RWC was calculated using the equation: RWC=(final weight–dry weight)/(initial weight–dry weight)×100. Xylem water potential was determined using Scholander pressure bomb technology.

Figure 7:
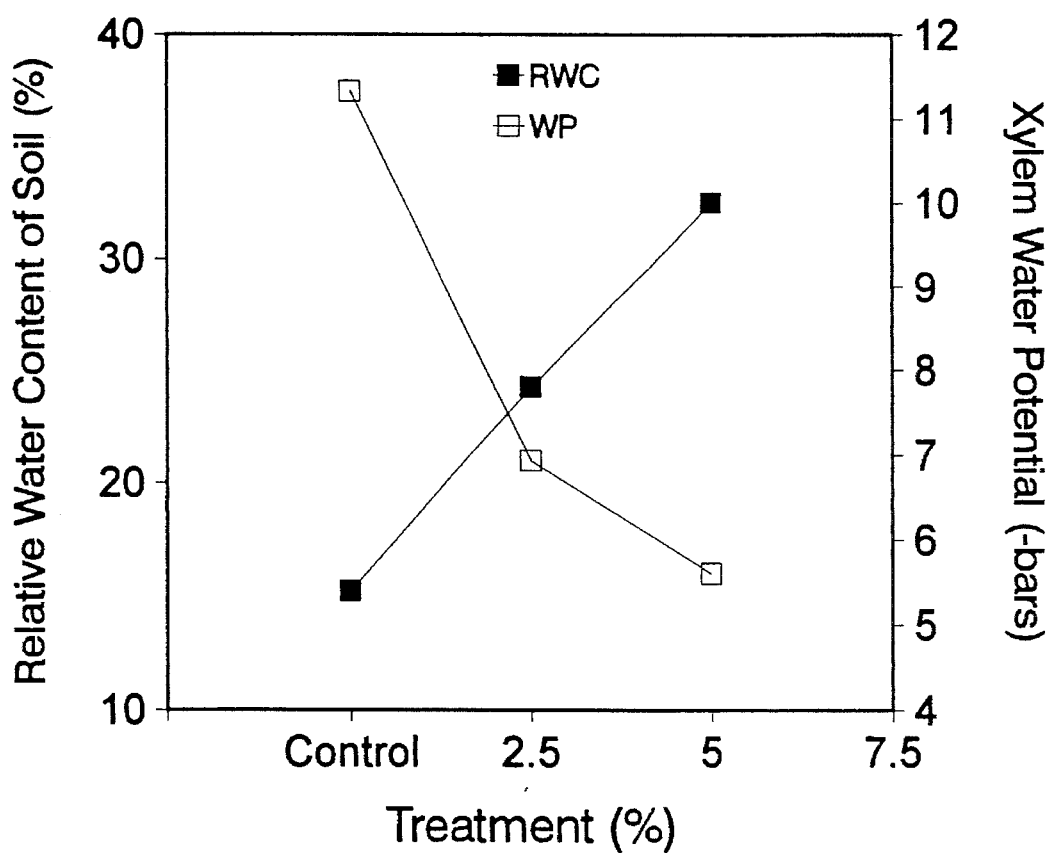
FIG. 7 is a graph of soil relative water potential (RWP) and xylem water potential (WP) for pepper stem tissue treated with aqueous solutions of 0%, 2.5%, and 5% sorbitol.

The results, illustrated by FIG. 7, show that the soil RWC for plants treated with the inventive composition is significantly greater than the soil RWC for control plants and increases with increasing concentration of sorbitol. The same is true with the xylem water potential. These results indicate that water consumption by the control plants is far greater than water consumption by the treated plants, while the water potentials of the treated plants are greater than the water potentials of the controls. The treated plants remained turgid and out-survived control plants under drought conditions.

EXAMPLE 5

Figure 8:
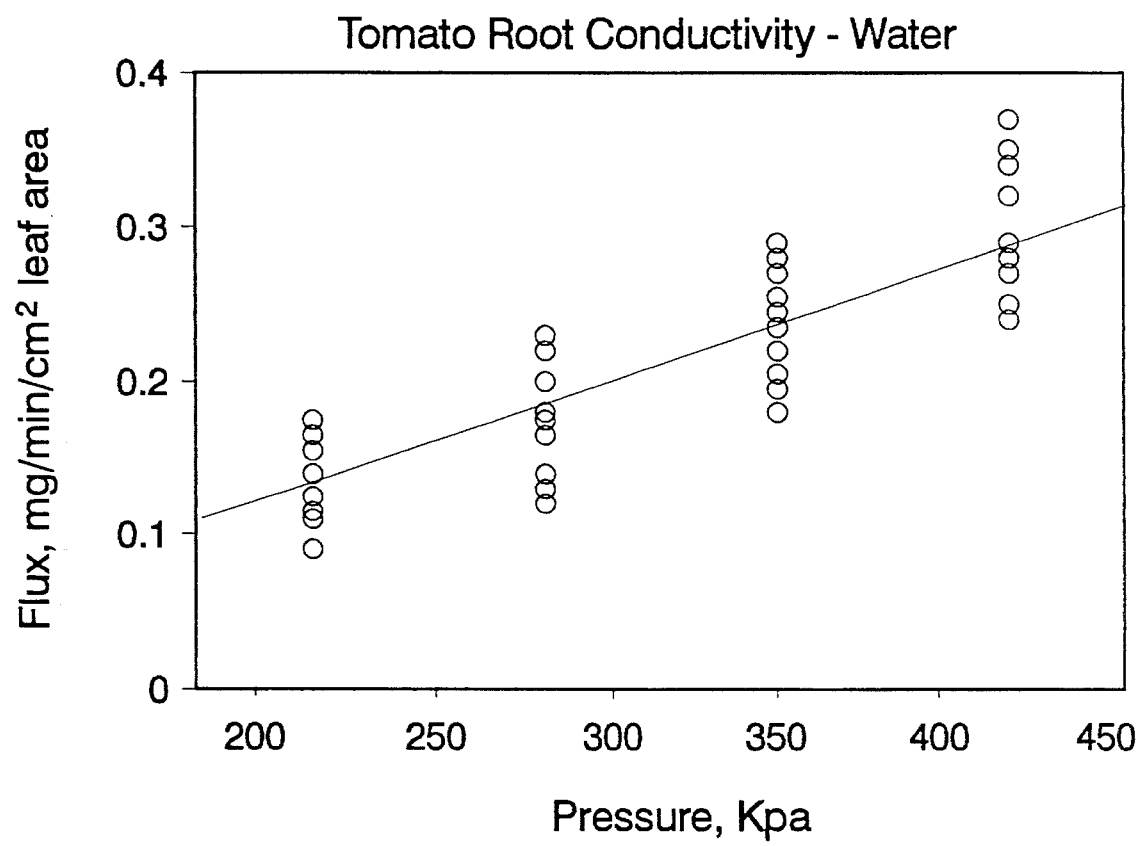
FIG. 8 illustrates root conductivity of tomato plants treated with water only.
Figure 9:
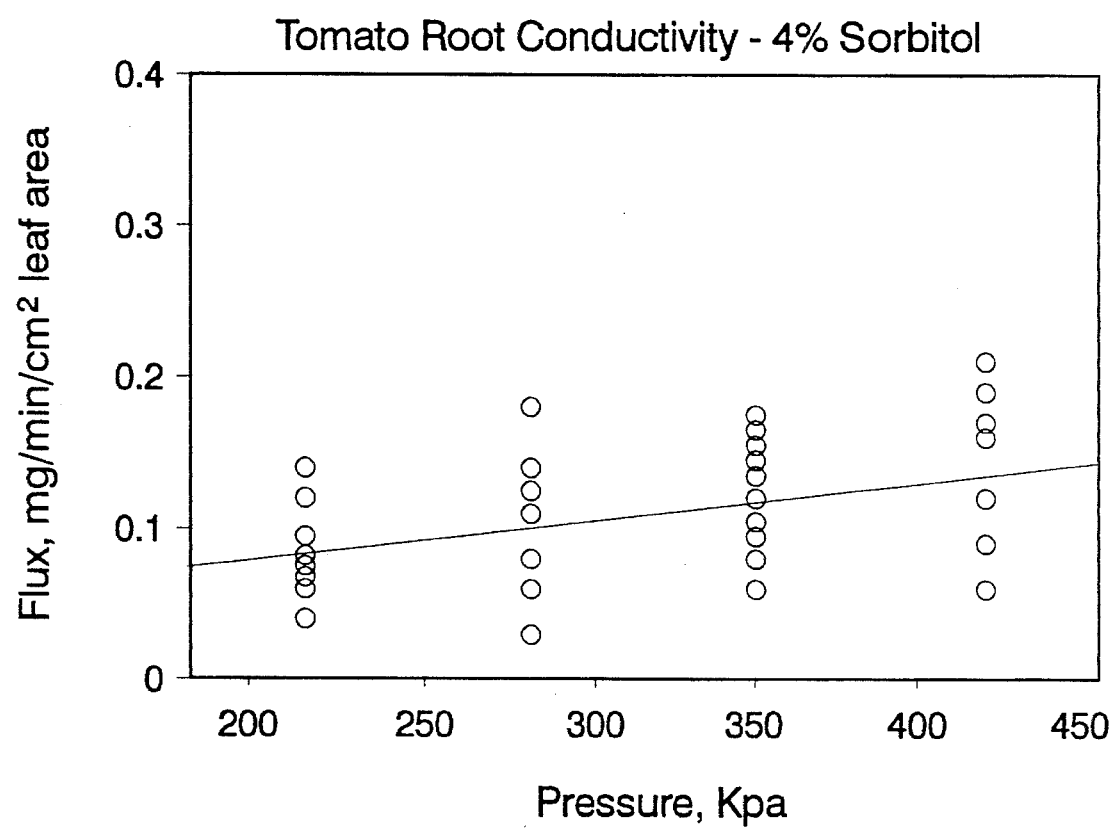
FIG. 9 illustrates root conductivity of tomato plants treated with aqueous solutions of 4% sorbitol.

The effectiveness of the present invention as a plant water consumption reducing agent is demonstrated by an experiment showing that the plants treated with an aqueous solution of 4% sorbitol reduces water uptake from soil media. The relative water movement of plant root system was determined by measuring root hydraulic conductivity of the plants, as shown in FIGS. 8–9.

Root drenching with a formulation of the present invention causes a large reduction in the hydraulic conductivity of tomato root membranes. The permeability of roots to water in treated plants in less than 50% of controls, when expressed on a unit leaf area basis.

EXAMPLE 6

The effectiveness of the present invention to preserve moisture content of the plant tissues is demonstrated by showing water loss rate from severed tomato seedlings.

Figure 10:
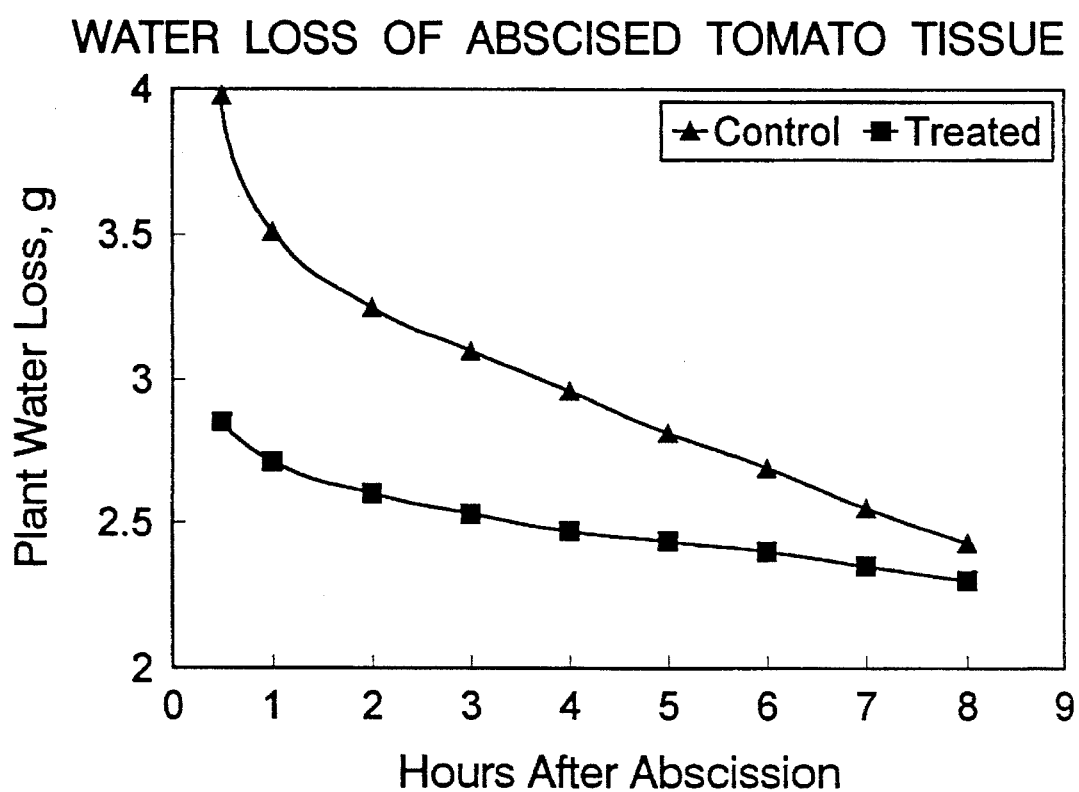
FIG. 10 illustrates water loss of abscised tomato tissues over time.

The shoots of tomato seedlings were cut at the base of the stem at 6:30 A.M. and water loss of the cut tissues was monitored every hour from 7:00 A.M. to 3:00 P.M. Experimental results are shown in FIG. 10.

The results show a significant difference in water retention of the detached tissue between the plants treated with an aqueous solution of 4% sorbitol and the control plants treated with DI water. This is true in spite of the virtual certainty that stomata would have been closed in both treated and non-treated plants within one hour after harvest.

EXAMPLE 7

Young bedding plants are suffering from desiccation during transportation from seedling growers to farmers. Several trays containing celery, lettuce, and watermelon seedlings drenched with aqueous solutions of 2.5% and 5% sorbitol a day before scheduled transportation. After making a round trip from Oregon state to Idaho state in June, 1993, the conditions of the seedlings were observed.

The bedding plant seedlings treated with formulations of the present invention suffered less than 5% damage and remained in a sellable condition, while the control plants suffered more than 50% damage from desiccation. The normal expected damage for one way transportation from Oregon to Idaho state is 30% to 40% during hot months of June and July.

EXAMPLE 8

Potted dwarf gardenia plants are produced under hot and humid condition in Florida. When shipped to other states, these plants are very sensitive to heat and desiccation. Two sets of 36 potted gardenia plants were root drenched with water only and aqueous solutions of 5% and 8% sorbitol a day before shipping to Medford, Oregon and Oregon State University. After withholding water for seven days, the plants were visually inspected and photographs were taken.

The gardenia plants treated with 5% and 8% remained turgid and green while the control plants became wilted and dry. This effectiveness was demonstrated at both locations (Medford and Corvalis, Oreg.).

EXAMPLE 9

The effectiveness of the present invention as an agent to extend shelf life of potted plants was tested on marigold, poinsettia, impatiens, gardenia, fuschsia, dwarf rose, and hemlock trees with applications of aqueous solutions of various concentrations or sorbitol. The applications extended shelf life of the plants tested. The treated plants stayed turgid and green much longer than the control plants.

EXAMPLE 10

The efficacy of the present invention in enabling plants to avoid drought stress is demonstrated by experiments showing that three species of young conifer seedlings treated with aqueous solutions of various concentrations of sorbitol lose significantly less water than do seedlings treated with water only.

Six-month old, greenhouse grown Douglas fir, western hemlock, and western cedar in 60 ml styro-block containers were placed in a greenhouse to acclimate to a new environment. The plants were treated in six different ways: a well watered control, non-watered control, aqueous solutions of 2.5%, 5%, 10%, and 20% sorbitol. All seedlings were watered to field capacity one day prior to the treatment of 10 ml of each solution. The non-watered seedlings also received 10 ml DI water in a similar manner. Water was then withheld from the seedlings of 5 treatments for the duration of the experiment. The well watered seedlings were watered to field capacity every other day for the duration of the experiment. Stomatal conductance, water potential and water loss were measured. Photographs were taken as symptoms appeared.

Stomatal conductance on sorbitol treated seedlings was reduced when compared to the well watered control. However, the levels were not as much as the non-watered controls. Water potential of the seedlings followed a similar pattern with the sorbitol treated seedlings becoming a more negative relative to well watered controls, but not reaching a level as low as the non-watered controls. The weight of sorbitol treated seedlings was decreasing at a much slower rate then compared to the non-watered controls.

Foliage discoloration, sunken bark, and mortality were noted on the non-watered controls at least one week prior to sorbitol treated seedlings. The appearance of dead and desiccated foliage generally followed treatment concentrations with the higher concentrations maintaining a healthy appearance for several days longer.

EXAMPLE 11

The effectiveness of the present invention as an agent to aid rooting of cuttings is demonstrated by experiments showing that dry root weight of sorbitol treated ivy cuttings is more than 50% heavier than control rooted cuttings.

Ivy mother plants (Ivy stock plants) were root drenched with aqueous solutions of 5% and 8% sorbitol a day prior to cutting. The cuttings were placed in a mist chamber to root for 30 days. The cuttings were then removed from the mist chamber and allowed to grow for 20 days in a greenhouse. Roots from five plants from each treatment were sampled, dried, and weighed.

The total dry root weights for the rooted cuttings from control, 5% sorbitol treated, and 8% sorbitol treated plants were 652, 1019, and 995 mg, respectively. Weight increase in dry root weight of the rooted cutting from 5% and 8% sorbitol treated mother plants were 56.3% and 52.5% over the control dry root weight.

EXAMPLE 12

The effectiveness of the present invention as a plant water reducing agent on monocotyledon plants was demonstrated by an experiment showing that the treated turf grass stayed green for 20 days while withholding water.

Two different cultivar sods, Palmer Rye (sunny grass) and Red Fescue (shady grass), were developed from seed on trays and water was withheld for 20 days before normal watering resumed. The sods treated with water only, started to turn brown and did not survive the water shortage.

EXAMPLE 13

The effectiveness of the present invention as an agent to condition (acclimate) plants against environmental stress is evidenced by experiments showing that tomato plants treated with an aqueous solution of 4% sorbitol accumulate higher solute and total ion concentrations in leaf sap than the plants treated with the same volume of DI water only. This is true for both irrigated and non-irrigated plants. The increases observed in individual ions are small, but taken together result in a significant increase of total ion concentration.

Figure 11:
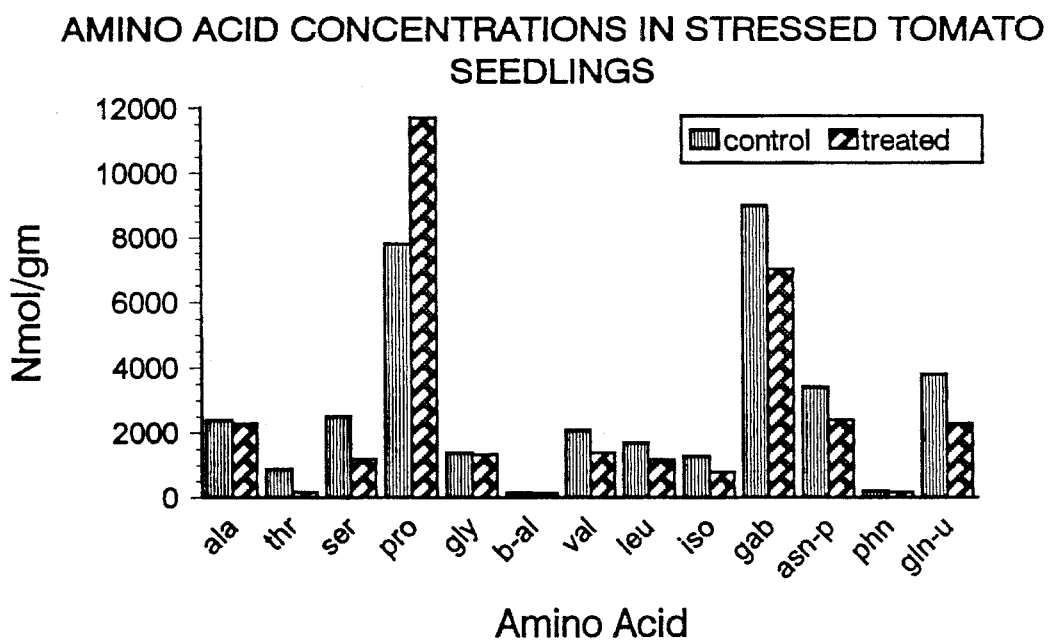
FIG. 11 shows amino acid concentrations for irrigated tomato seedlings.
Figure 12:
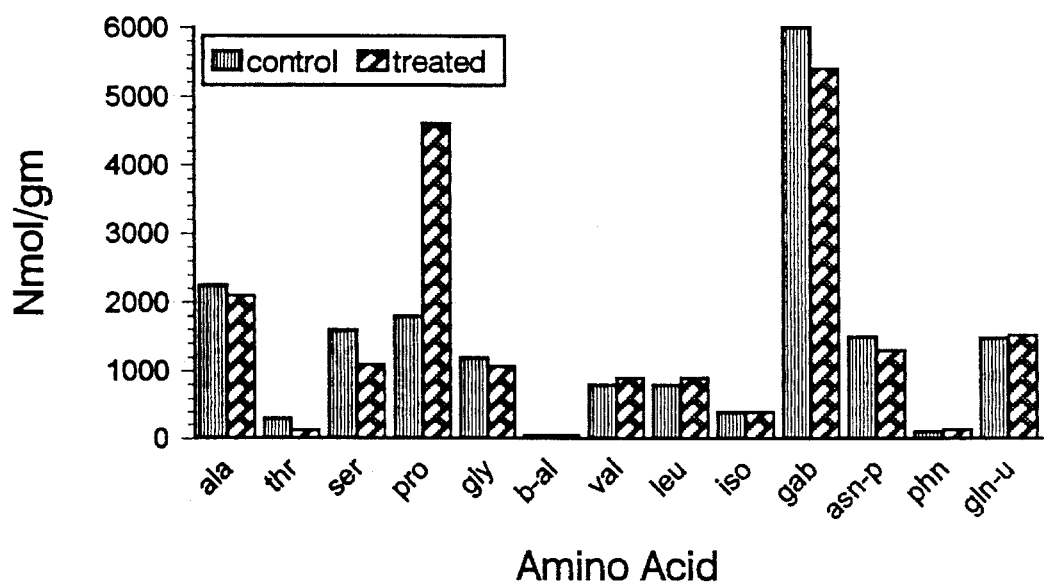
FIG. 12 shows amino acid concentrations for non-irrigated tomato seedlings.

The solutes analyzed account for 75% to 80% of the total osmolality. The missing solutes likely include amino acids, organic acids, and other ions not analyzed (e.g. anions). The high increase in organic solute concentrations, especially sugar concentrations indicates that root drenching with an aqueous solution of 4% sorbitol induce osmo-adjustment. The concentrations of various amino acids in the missing solutes were further analyzed as shown in FIG. 11.

One result is that sorbitol induces substantial increases in proline concentration of leaf sap. This is observed in both stressed (non-irrigated) and non-stressed (irrigated) plants. Proline can ameliorate the deleterious effects of high temperature, salt, and dehydration on enzyme activity and organelle systems.

TABLE 2

Concentrations of Metabolites in Leaf Saps From 5 Weeks Old Tontato Plants 4 Days After Treatment With Aqueous Solutions of 0% and 4% Sorbitol

|  | IRRIGATED | | NON-IRRIGATED | |
| --- | --- | --- | --- | --- |
|  | DI Water | Sorbitol | DI Water | Sorbitol |
| P | 20.4 | 20.0 | 20.8 | 24.9* |
| Mg | 24.9 | 28.3* | 29.9 | 35.5* |
| Ca | 23.4 | 38.6* | 33.4 | 43.2 |
| Na | 9.7 | 12.5 | 11.8 | 15.0* |
| K | 133.0 | 137.1* | 147.1 | 164.5* |
| Total Ions | 211.4 | 236.5* | 243.0 | 283.3* |
| Sugars | 68.1 | 97.3* | 56.5 | 109.0* |
| Total Solutes | 79.5 | 333.7* | 294.6 | 392.2* |
| Osmolality | 47.4 | 436.0* | 388.4 | 512   4* |
| Solutes Missing | 67.9 | 102.3* | 93.8 | 120:2* |
| W. Potential | 7.5 | 9.5* | 12.5 | 13.6* |

*Statistically significant change

EXAMPLE 14

The efficacy of the present invention is also demonstrated by experiments showing that the plants conditioned with the present invention are hardier against drought stress. A set of four tomato plants per each treatment including control was transplanted to 4 inch (in diameter) pot 29 days after the last treatment. After uniform soil water conditions were established, watering was stopped for a week.

Tomato plants conditioned 31 days prior to the water denial remained turgid and have dark green leaves while unconditioned plants (control plants) are severely wilted.

This long-lasting conditioning effect has been confirmed by an outside university evaluation. A set of 22 week old and plug-grown seedlings was treated with two sequential applications of an aqueous solution of 1% sorbitol. The treated plants exhibited a very rapid growth inhibition relative to the control plants. The difference was apparent within several days. After an additional two weeks, the plants in the plugs were transplanted into 6 inch standard pots to evaluate seedling response to water stress. After soil water conditions were established, water was withheld and plants were observed daily to evaluate the effects of the present invention. After ten days without water, the difference between treated and control seedlings was remarkable and distinct. Untreated plants were severely wilted, while treated plants remained turgid and had dark green leaves. There was no lasting growth inhibition, however, and time differences in leaf turgor do not appear to be related to differences in plant size.

It is to be appreciated that the compositions of the present invention may effectively be used on plants to reduce water loss, ho induce stomatal closing, to reduce transpiration rates, to avoid drought stress, to aid in rooting cuttings, to extend shelf life of container plants, to avoid transportation stress, to reduce root uptake and preserve soil moisture, to reduce water loss of severed plant tissue, to condition plants for drought stress avoidance, to reduce transplanting stress, and to act as an antidesiccant. It is further to be appreciated that the effectiveness is universal, applying to mono- and di-cotolyedon plants, to conifers and deciduous trees, to bedding plants and to vegetables.

While the invention has been described in detail in the foregoing description, the same is to be considered as illustrative and not restrictive in character, it being understood that only the preferred embodiment has been shown and described and that all changes and modifications that come within the spirit of the invention are desired to be protected.

What is claimed is:

1. A method of reducing water loss from plant tissue, comprising applying to the root zone of the plant a solution consisting essentially of a water loss reducingly effective amount of an osmo-adjusting solute selected from the group consisting of sorbitol and xylitol.

2. The method of claim 1 wherein the solution is applied to the plant's root zone by drenching regularly or prior to water deficiency.

3. The method of claim 1 wherein the solution includes between about 0.05 and about 25 weight percent of the water loss reducing composition.

4. The method of claim 3 wherein the solution includes between about 0.5 and about 10 weight percent of the water loss reducing composition.

5. A method of reducing the transpiration rate of plants, comprising applying to the root zone of the plant an effective amount of a solution consisting essentially of a composition selected from the group consisting of sorbitol and xylitol.

6. A method of inducing stomatal closing of plants, composition applying to the root zone of the plant an effective amount of a solution consisting essentially of a composition selected from the group consisting of sorbitol and xylitol.

7. A method of avoiding drought stress for plants, comprising applying to the root zone of the plant an effective amount of a solution consisting essentially of a solvent and a composition selected from the group consisting of sorbitol and xylitol.

8. A method of extending the shelf life of container plants, comprising applying to the root zone of the plant an effective amount of a solution consisting essentially of a solvent and a composition selected from the group consisting of sorbitol and xylitol.

9. A method of avoiding transportation stress to plants, comprising applying to the root zone of the plant and absorbing into the plant tissue an effective amount of a solution consisting essentially of a solvent and a composition selected from the group consisting of sorbitol and xylitol.

10. A method of reducing water loss from severed plant tissue, comprising applying to the root zone of the plant prior to the severation an effective amount of a solution consisting essentially of a solvent and a composition selected from the group consisting of sorbitol and xylitol.

11. A method of conditioning plants to avoid drought stress, comprising applying to the root zone of the plant an effective amount of a solution consisting essentially of a solvent and a composition selected from the group consisting of sorbitol and xylitol.

12. A method of reducing transplanting stress to plants, comprising applying to the root zone of the plant an effective amount of a solution consisting essentially of a solvent and a composition selected from the group consisting of sorbitol and xylitol.

13. A method of extending the turgidity of cuttings taken from a stock plant for better root development, comprising applying to the root zone of the stock plant an effective amount of a solution consisting essentially of a solvent and a composition selected from the group consisting of sorbitol and xylitol.

14. The method of claim 1 in which said applying comprises root drenching, drip irrigating or direct soaking of the plant roots followed by absorbing of the composition into the plant tissue.

\* \* \* \* \*

UNITED STATES PATENT AND TRADEMARK OFFICE
CERTIFICATE OF CORRECTION

PATENT NO. : 5,459,121
DATED : October 17, 1995
INVENTOR(S) : Charles C. Shin; Nicolai A. Favstritsky; Brent M. Sanders It is certified that error appears in the above-indentified patent and that said Letters Patent is hereby corrected as shown below:

```
In column 2, line 10, please change "arid" to --and--.
In column 4, line 2, please change "tile" to --the--.
In column 5, line 28, please change "tile" to --the--.
In column 5, line 60, please change "tile" to --the--.
In column 8, Table 2, line 63, please change "512  4*" to --512.4*--.
In column 8, Table 2, line 64, please change "120:2*" to --120.2*--.
In column 9, line 28, please change "time" to --the--.
In column 9, line 33, please change "ho" to --to--.
```

Signed and Sealed this

Fifth Day of March, 1996

*Attest:*

BRUCE LEHMAN

*Attesting Officer*   Commissioner of Patents and Trademarks